US008518981B2

(12) United States Patent
Calderari et al.

(10) Patent No.: US 8,518,981 B2
(45) Date of Patent: *Aug. 27, 2013

(54) LIQUID PHARMACEUTICAL FORMULATIONS OF PALONOSETRON

(75) Inventors: Giorgio Calderari, Rancate (CH); Daniele Bonadeo, Varese (IT); Roberta Cannella, Varese (IT); Andrew Miksztal, Palo Alto, CA (US); Thomas Malefyt, Carmel Valley, CA (US); Kathleen Lee, Palo Alto, CA (US)

(73) Assignees: Helsinn Healthcare SA, Lugano/Pazzallo (CH); Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/087,012

(22) Filed: Apr. 14, 2011

(65) Prior Publication Data

US 2011/0192493 A1    Aug. 11, 2011

Related U.S. Application Data

(63) Continuation of application No. 11/186,311, filed on Jul. 21, 2005, now Pat. No. 7,947,724, which is a continuation of application No. PCT/EP2004/000888, filed on Jan. 30, 2004.

(60) Provisional application No. 60/444,351, filed on Jan. 30, 2003.

(51) Int. Cl.
*A01N 43/52* (2006.01)

(52) U.S. Cl.
USPC .......................................................... 514/397

(58) Field of Classification Search
USPC .......................................................... 514/397
See application file for complete search history.

(56) References Cited

U.S. PATENT DOCUMENTS

| | | | |
|---|---|---|---|
| 4,695,578 A | 9/1987 | Coates et al. |
| 4,753,789 A | 6/1988 | Tyers et al. |
| 4,886,808 A | 12/1989 | King |
| 4,906,755 A | 3/1990 | Gittos |
| 4,929,632 A | 5/1990 | Tyers et al. |
| 4,937,247 A | 6/1990 | King |
| 5,011,846 A | 4/1991 | Gittos et al. |
| 5,034,398 A | 7/1991 | King |
| 5,202,333 A | 4/1993 | Berger et al. |
| 5,240,954 A | 8/1993 | Tyers et al. |
| 5,272,137 A | 12/1993 | Blase et al. |
| 5,344,658 A | 9/1994 | Collin |
| 5,578,628 A | 11/1996 | Tyers et al. |
| 5,578,632 A | 11/1996 | Tyers et al. |
| 5,622,720 A | 4/1997 | Collin |
| 5,854,270 A | 12/1998 | Gambhir |
| 5,922,749 A | 7/1999 | Tyers et al. |
| 5,955,488 A | 9/1999 | Winterborn |
| 6,063,802 A | 5/2000 | Winterborn |
| 6,132,758 A | 10/2000 | Munayyer et al. |
| 6,284,749 B1 | 9/2001 | Castillo et al. |
| 6,287,592 B1 | 9/2001 | Dickinson |
| 6,294,548 B1 | 9/2001 | James |
| 6,699,852 B2 | 3/2004 | Robichaud |
| 7,109,339 B2 | 9/2006 | Lee et al. |
| 7,947,724 B2 | 5/2011 | Calderari et al. |
| 7,947,725 B2 | 5/2011 | Calderari et al. |
| 7,960,424 B2 | 6/2011 | Calderari et al. |
| 2001/0020029 A1 | 9/2001 | James |
| 2003/0095926 A1 | 5/2003 | Dugger, III |

FOREIGN PATENT DOCUMENTS

| | | |
|---|---|---|
| EP | 0 512 400 A1 | 4/1992 |
| WO | 03/100091 | 12/2003 |
| WO | 2004045615 | 6/2004 |
| WO | 2004067005 | 8/2004 |
| WO | 2004703714 | 9/2004 |

OTHER PUBLICATIONS

Opposition Brief filed by Dr. Reddy's Laboratories (UK) Limited, opposition to European Patent No. 1601359 B1, Jul. 7, 2009.
Photolytic and oxidative degradation of an antiemetic agent, RG 12915 (Won C. M. Et al, International Journal of Pharmaceutics 121 (1995) 95-105 (1995).
Palonosetron: a phase II dose ranging study to assess over a 7 day period the single dose pharmacokinetic profile of palonosetron in patients receiving highly emetogenic chemotherapy. Piraccini Get al., Proc. Am. Soc. Clin. Oncol 2002 21 Abs 449 (2002).
Formulation and administration techniques to minimize injection pain and tissue damage associated with parenteral products. Larry A. Gatlin; Carol A Brister Gatlin, [from Injectable Drug Development: Techniques to Reduce Pain and Irritation [Edited by Pramod K. Gupta, Gayle A. Brazeau; Published by Informa Health Care (original copyright of 1999 by Interpharma Press), 1999; ISBN 1574910957, 9781574910957)], p. 401-421.
Parenteral Dosage Forms. Joanne Broadhead. [from Part 11—Early drug development, Pharmaceutical preformulation and formulation: a practice guide from candidate drug selection to commercial dosage form [Edited by Mark Gibson; Published by Interpharma Press, 2001; ISBN 1574911201, 9781574911206)], p. 331-353.
Opposition Brief filed by Tecnimede Sociedade Tecnico-Medicinal S.A., opposition to European Patent No. 1601359 B1, Jul. 8, 2009.
Response brief filed by Helsinn Healthcare S.A. dated Jul. 13, 2007, in response to the communication pursuant to Art. 96(2) EPC of Jan. 3, 2007 regarding Serial No. 04 706 657.6-2123.
European Patent Office official communication dated Jul. 19, 2006 regarding U.S. Appl. No. 04 706 657.6.
Response of Helsinn Healthcare S.A. dated Nov. 29, 2006 regarding EPO official communication dated Jul. 19, 2006.
Lachman et al., The Theory and Practice of Industrial Pharmacy, 1986, third edition, pp. 652-784.
Summary of Product Characteristics for Aloxi 250 (2009).
Declaration of Valentino J. Stella, Ph.D. dated Sep. 19, 2007.

(Continued)

*Primary Examiner* — Shirley V Gembeh

(74) *Attorney, Agent, or Firm* — Arnall Golden Gregory LLP; Clark G. Sullivan; Kimberly Bond

(57) ABSTRACT

The present invention relates to shelf-stable liquid formulations of palonosetron for reducing chemotherapy and radiotherapy induced emesis with palonosetron. The formulations are particularly useful in the preparation of intravenous and oral liquid medicaments.

12 Claims, No Drawings

(56) References Cited

OTHER PUBLICATIONS

Opposition Brief filed by Martin Paul White, opposition to European Patent No. 1601359 B1, Jul. 8, 2009.
Wong et al. (1995), in British Journal of Pharmacology, vol. 114, pp. 851-859 and Eglen et al. (1995), in British Journal of Pharmacology, vol. 114, pp. 860-866.
Cover page and pp. 642-644 and 783-784 of The Theory and Practice of Industrial Pharmacy, Third Edition, Lea and Febiger (1986).
Cover page and pp. 514-515 of Modern Pharmaceutics, Second Edition, Marcel Dekker (1990).
Cover page and pp. 142-143 of Pharmaceutical Dosage Forms: Parenteral Medications vol. 1, Second Edition, Marcel Dekker (1992).
Scientific Discussion from the European Public Assessment Report for Aloxi (Palonosetron Hydrochloride) (2006).
Mitsuo Matsumoto, et al., "Yakuzaigaku Manual", 1st edition, Nanzando Co., Ltd. (1989) 2 pages.
Michael J. Pikal, "Freeze Drying", Encyclopedia of Pharmaceutical Technology, Third Edition, Jan. 2007, pp. 1824-1825, vol. 3, Informa Pharmaceuticals & Healthcare.
Daniele Bonadeo, "Supplemental Declaration of Daniele Bonadeo 37 C.F.R. 1.132", U.S. Appl. No. 11/388,270, filed Jun. 8, 2009.
Kranke et al. 2007, "Recent advances, trends and economic considerations in . . . " Expert Opinion Pharmacother., 8 (18): 3217-3235).
Morrow et al. 1995, Progress in reducing nausea and emesis. Comparisons of ondansetron, granisetron, and tropisetron. Cancer, vol. 76 No. 3 pp. 343-357.
USPTO Notice of Allowance and Fee Due, U.S. Appl. No. 11/388,270, filed Mar. 24, 2006, Date Mailed Jan. 26, 2010.
USPTO Office Action, U.S. Appl. No. 11/129,839, Date Mailed Jan. 15, 2010.
Israili, Zafar H., Clinical Pharmacology of Serotonin Receptor Type-3 (5-HT3) Antagonists, Curr. Med. Chern.—Central Nervous System Agents, 2001, 1, 171-199.
Barton (Citrate Buffer Calculation), 2000, 2 pages.
USPTO Office Action, U.S. Appl. No. 11/201,035, Date Mailed Aug. 19, 2009.
Response of Helsinn Healthcare to opposition of EP Serial No. 04 706 657.6 dated Feb. 11, 2010.
Annex 1 (Statement of Waldo Mossi, Ph.D.) to Response of Helsinn Healthcare to opposition of EP Serial No. 04 706 657.6 dated Feb. 11, 2010.
Annex 2 to Response of Helsinn Healthcare to opposition of EP Serial No. 04 706 657.6 dated Feb. 11, 2010.
Annex 3 to Response of Helsinn Healthcare to opposition of EP Serial No. 04 706 657.6 dated Feb. 11, 2010.
6th Edition, Handbook of Pharmaceutical Excipients (2009), pp. 247-250n (RPS Publishing).
USPTO Office Action, U.S. Appl. No. 11/388,268, filed Mar. 24, 2006, Mail Date Mar. 29, 2010.
Lewis, Gareth A (2006), 'Optimization Methods,' Encyclopedia of Pharmaceutical Technology, 1: 1, 2452-2467.
Chelly, Jacques et al., Oral RS-25259 Prevents Postoperative Nausea and Vomiting Following Laparoscopic Surgery, extracted from Anesthesiology, 1996, vol. 85 No. 3A. p. A21.
Sorbe, Bengt, 5-HT3 Receptor Antagonists as Antiemetic Agents in Cancer Chemotherapy, extracted from Expert Opinion on Investigational Drugs, 1996, vol. 5 No. 4, pp. 389-407.
Gaster, Laramie M. and King, Frank D., Serotonin 5-HT3 and 5-HT4 Receptor Antagonists, extracted from Medicinal Research Reviews, 1997 vol. 17, No. 2, pp. 163-214.
Tang, Jun et al., Efficacy of RS-25259, a Novel 5-HT3 Antagonist, in the Prevention of Postoperative Nausea and Vomiting After Major Gynecologic Surgery, abstract extracted from Anesthesiology, 1997, vol. 85, No. 3, suppl. p. A329.
Tang, Jun et al., The Efficacy of RS-25259, a Long-Acting Selective 5-HT3 Receptor Antagonist, for Preventing Postoperative Nausea and Vomiting After Hysterectomy Procedures, extracted from Anesthesia and Analgesia, 1998, vol. 87, pp. 462-467.

Adis R&D Profile, Palonosetron RS 25259, RS 25259 197, extracted from Drugs in R&D, Oct. 1999, vol. 2, No. 4, pp. 251-252.
Piraccini, Gaia et al., An Interesting 5-HT3 Receptor Antagonist Antiemetic for Patients Undergoing Chemotherapy-Based Conditioning Regimens?, extracted from Blood, Nov. 16, 2001, vol. 98, No. 11, part 2, p. 350b, abstract No. 5169.
Stacher, Georg, Palonosetron Helsinn, extracted from Current Opinion in Investigational Drugs, Oct. 2002, vol. 3, No. 10, pp. 1502-1507.
Navari, Rudolph M., Pathogenesis-Based Treatment of Chemotherapy-Induced Nausea and Vomiting—Two New Agents, extracted from Journal a/Supportive Oncology, 2003, vol. 1(2), pp. 89-103.
Chaitow, 1990, 3 pages.
Jun. 8, 2009 Bonadeo Declaration.
Jun. 8, 2009 Bonadeo Declaration, Exhibit 2.
Jun. 8, 2009 Bonadeo Declaration, Exhibit 3.
HELSN0117262-69, (2008).
HELSN0117270-312, (2012).
Feb. 13, 2007 Statutory Declaration of Daniele Bonadeo, with Exhibit A.
Nov. 21, 2007 Statutory Declaration of Giorgio Calderari, Daniele Bonadeo, Roberta Cannella, Enrico Braglia, and Riccardo Braglia.
Reddy's Paragraph IV notice regarding all three patents (D. N.J. Case No. 12-2867), Mar. 30, 2012.
May 11, 2012 Complaint for patent infringement filed by Helsinn and Roche (D. N.J. Case No. 12-2867).
Jun. 26, 2012 Notice of Reddy's motion to dismiss (D. N.J. Case No. 12-2867).
Jun. 26, 2012 Dr. Reddy's Laboratories, Ltd.'s and Dr. Reddy's Laboratories, Inc.'s memorandum of law in support of their motion to dismiss or for summary judgment of non-infringement of U.S. patent No. 7,947,724 (D. N.J. Case No. 12-2867) (including Exhibits 1-10).
Aug. 16, 2012 Notice of Plaintiffs' cross-motion for partial summary judgment of infringement (D. N.J. Case No. 12-2867).
Aug. 6, 2012, Plaintiffs' opposition to Defendants' motion to dismiss or for summary judgment of noninfringement and cross-motion for partial summary judgment of infringement (D. N.J. Case No. 12-2867) (including exhibits 1-4).
Schöneich declaration (D. N.J. Case No. 12-2867) (Including Exhibits A and 1-24), (Aug. 6, 2012).
Sep. 4, 2012 Reddy's brief in opposition to Plaintiffs' cross-motion for partial summary judgment and reply memorandum of law in further support of Reddy's motion to dismiss or for summary judgment of non-infringement (D. N.J. Case No. 12-2867) (Including Exhibits 1-4).
DeLuca Declaration (D. N.J. Case No. 12-2867) (Including exhibits A-J) (Sep. 20, 2012).
Sep. 10, 2012 Plaintiffs' letter to Judge Cooper in response to Reddy's combined opposition to Plaintiffs' cross-motion for partial summary judgment and reply in support of Reddy's motion to dismiss or for summary judgment of noninfringement (D. N.J. Case No. 12-2867) (including exhibits A and B).
Sep. 14, 2012 Dr. Reddy's letter in response to Plaintiffs' Sep. 10, 2012 letter (D. N.J. Case No. 12-2867).
May 24, 2011 Para. IV notice from Teva Pharmaceuticals re '724 and '725 patents.
May 24, 2011 Para. IV notice from Sandoz re '724 and '725 patents.
May 24, 2011 Para. IV notice from Dr. Reddy's re '724 and '725 patents.
Aug. 9, 2011 Para. IV notice from Dr. Reddy's re '424 patent.
Aug. 19, 2011 Para. IV notice from Teva Pharmaceuticals re '424 patent.
Sep. 22, 2011 Para. IV notice from Sandoz re '724, '725 and '424 patents.
Jul. 8, 2011 Complaint for patent infringement (D. N.J. case No. 11-03962).
Sep. 23, 2011 Complaint for patent infringement (D. N.J. case No. 11-5579).
Aug. 31, 2011 Answer and counterclaim of Dr. Reddy's Laboratories, Ltd. and Dr. Reddy's Laboratories, Inc. (D. N.J. case No. 11-03962).
Sep. 13, 2011 Sandoz Inc.'s answer to complaint for patent infringement and counterclaims (D. N.J. case No. 11-03962).

Sep. 13, 2011 Teva Pharmaceuticals USA, Inc. and Teva Pharmaceutical Industries Ltd.'s answer (D. N.J. case No. 11-03962).
Oct. 5, 2011 Plaintiffs' reply to answer and counterclaim of Dr. Reddy's Laboratories, Ltd. and Dr. Reddy Laboratories, Inc. (D. NJ. case No. 11-03962).
Oct. 21, 2011 Plaintiffs' reply to Sandoz Inc.'s answer to complaint for patent infringement and counterclaims (D. N.J. case No. 11-03962).
Oct. 24, 2011 Answer and counterclaim of Dr. Reddy's Laboratories, Ltd. and Dr. Reddy's Laboratories, Inc. (D. N.J. case No. 11-5579).
Oct. 24, 2011 Sandoz Inc.'s answer to complaint for patent infringement and counterclaims (D. N.J. case No. 11-5579).
Oct. 27, 2011 Order consolidating the two cases (D. N.J. case No. 11-5579).
Nov. 17, 2011 Plaintiffs' reply to answer and counterclaim of Dr. Reddy's Laboratories, Ltd. and Dr. Reddy's Laboratories, Inc. (D. N.J. case No. 11-03962).
Nov. 17, 2011 Plaintiffs' reply to Sandoz Inc.'s answer to complaint for patent infringement and counterclaims (D. N.J. case No. 11-03962).
Dec. 5, 2011 Teva Pharmaceuticals USA Inc. and Teva Pharmaceuticals Industries Ltd.'s answer to complaint for patent infringement of the '424 patent (D. N.J. case No. 11-03962).
May 21, 2012 Defendants' opening claim construction brief (including exhibits 1-31).
May 21, 2012 Plaintiffs' opening claim construction brief (including exhibits 1-15).
Jul. 20, 2012 Defendants' responsive claim construction brief (including exhibits 1-3).
Jul. 20, 2012 Plaintiffs' responsive claim construction brief (including Exhibits A and B).
Sep. 7, 2012 Court transcript from Sep. 7, 2012 Markman hearing and Plaintiffs' PowerPoint presentation (D. N.J. case No. 11-03962).
Dec. 1, 2011 Sandoz Inc.'s invalidity contentions pursuant to L. Pat. R. 3.6(c) (D. N.J. case No. 11-03962).
Dec. 1, 2011 Teva Pharmaceuticals USA, Inc. and Teva Pharmaceutical Industries, Ltd.'s invalidity contentions pursuant to L. Pat. R. 3.6(c) (D. N.J. case No. 11-03962).
Dec. 1, 2011 Dr. Reddy's Laboratories, Ltd.'s and Dr. Reddy's Laboratories, Inc.'s invalidity contentions pursuant to L. Pat. R. 3.6(c) (D. N.J. case No. 11-03962).
Jan. 31, 2012 Plaintiffs' responses to defendants' invalidity contentions (D. N.J. case No. 11-03962).
Sep. 25, 2012 Sandoz Inc.'s first amended invalidity contentions pursuant to L. Pat. R. 3.6(c) (D. N.J. case No. 11-03962).
Nov. 19, 2012 Plaintiffs' responses to Sandoz Inc.'s first amended invalidity contentions (D. N.J. case No. 11-03962).
L.G. Wade Jr., Organic Chemistry, Ch. 19: Amines, pp. 867-936 (Prentice Hall 3d ed. 1995).
L. Lachman et al., The Theory and Practice of Industrial Pharmacy, pp. 642-644,783-784 (Lea & Febiger 3d ed. 1986).
P.P. DeLuca et al., Formulation of Small Volume Parenterals, in Pharmaceutical Dosage Forms: Parenteral Medications, vol. 1, Ch. 5, pp. 173-248 (Avis, Lieberman, Lachman eds., Marcel Dekker Inc. 2d ed. 1992).
C.M. Won et al., Photolytic and Oxidative Degradation of an Antiemetic Agent, RGI2915, Int'l J Pharmaceutics 121:95-105 (1995).
R.D. Clark et al., 2-(Quinuciidin-3-yl)pyrido[4,3-b]indol-l-ones and Isoquinolin-l-ones. Potent Conformationally Restricted 5-HT3 Receptor Antagonists, J Med. Chem. 36:2645-57 (1993).
L.A. Trissel, Drug Stability and Compatibility Issues, in Handbook on Injectable Drugs, pp. XI-XVI (ASHP 7th ed. 1992).
J. Broadhead, Parenteral Dosage Forms, in Pharmaceutical Preformulation and Formulation: A Practical Guide from Candidate Drug Selection to Commercial Dosage Form, Ch. 9, pp. 331-354 (Gibson ed., CRC Press 1st ed. 2001).
K.A. Connors et al., Chemical Stability of Pharmaceuticals: A Handbook for Pharmacists (John Wiley & Sons 2d ed. 1986).
ZOFRAN®, in The Physicians' Desk Reference, 1503-07 (5th ed. 2001).
ANZEMET®, in The Physicians' Desk Reference, pp. 680-683 (5th ed. 2001).

KYTRIL®, in The Physicians' Desk Reference, pp. 3104-3106 (5th ed. 2001).
L.A. Trissel, Ondansetron HCI, in Handbook on Injectable Drugs, pp. 683-688 (ASHP 7th ed. 1992).
NAVOBAN® (tropisetron HCI) Malaysian Prescribing Information (Sep. 2000).
KYTRIL® (granisetron HCI) South African Prescribing Information (Dec. 1993).
S. Motola and S. Agharkar, Preformulation Research of Parenteral Medications, in Pharmaceutical Dosage Forms: Parenteral Medications, vol. 1, Ch. 4, pp. 115-172 (Avis, Lieberman, Lachman eds., Marcel Dekker Inc. 2d ed. 1992).
J. Wells, Pharmaceutical Preformulation: The Physicochemical Properties of Drug Substances, Ch. 5: Drug Stability, pp. 152-191 (Ellis Horwood Ltd. 1988).
J. Swarbrick and Boylan, Encyclopedia of Pharmaceutical Technology, Excipients Chapter: Their Role in Parenteral Dosage Forms, vol. 19(2):137-172 (Marcel Dekker, Inc. 2000).
Handbook of Pharmaceutical Excipients, 3d Ed., (Kibbe ed. Pharmaceutical Press 2000); pp. 140-143, 191-194,324-328.
G. Stacher, Palonosetron (Helsinn), Curro Opin. Investig. Drugs, 3(10) 1502-7 (2002).
Handbook of Modern Pharmaceutical Analysis, (S. Ahuja et al. eds., Academic Press, 2001).
USPTO Non-Final Office Action, U.S. Appl. No. 11/186,311, mailed Aug. 30, 2006.
USPTO Non-Final Office Action, U.S. Appl. No. 11/186,311, mailed Oct. 5, 2007.
USPTO Non-Final Office Action, U.S. Appl. No. 11/186,311, mailed Oct. 6, 2008.
USPTO Final Office Action, U.S. Appl. No. 11/186,311, mailed May 20, 2009.
USPTO Advisory Action, U.S. Appl. No. 11/186,311, mailed Jul. 15, 2009.
USPTO Notice of Allowance and Fees Due, U.S. Appl. No. 11/186,311, mailed Mar. 4, 2011.
USPTO Notice of Allowability, U.S. Appl. No. 11/186,311, dated May 24, 2011.
USPTO Non-Final Office Action, U.S. Appl. No. 11/388,268, mailed Jul. 17, 2006.
USPTO Non-Final Office Action, U.S. Appl. No. 11/388,268, mailed Nov. 17, 2006.
USPTO Non-Final Office Action, U.S. Appl. No. 11/388,268, mailed Oct. 3, 2007.
USPTO Non-Final Office Action, U.S. Appl. No. 11/388,268, mailed Mar. 26, 2008.
USPTO Final Office Action, U.S. Appl. No. 11/388,268, mailed Nov. 12, 2008.
USPTO Non-Final Office Action, U.S. Appl. No. 11/388,268, mailed Jul. 15, 2009.
USPTO Notice of Allowance and Fees Due, U.S. Appl. No. 11/388,268, mailed Dec. 22, 2010.
USPTO Non-Final Office Action, U.S. Appl. No. 11/388,269, mailed Jul. 19, 2006.
USPTO Non-Final Office Action, U.S. Appl. No. 11/388,269, mailed Nov. 17, 2006.
USPTO Non-Final Office Action, U.S. Appl. No. 11/388,269, mailed Sep. 20, 2007.
USPTO Non-Final Office Action, U.S. Appl. No. 11/388,269, mailed Jul. 9, 2008.
USPTO Interview Summary, U.S. Appl. No. 11/388,269, dated Apr. 28, 2009.
USPTO Final Office Action, U.S. Appl. No. 11/388,269, mailed May 20, 2009.
USPTO Advisory Action, U.S. Appl. No. 11/388,269, mailed Jul. 15, 2009.
USPTO Notice of Abandonment, U.S. Appl. No. 11/388,269, mailed Dec. 18, 2009.
USPTO Non-Final Office Action, U.S. Appl. No. 11/388,270, mailed Jul. 13, 2006.
USPTO Interview Summary, U.S. Appl. No. 11/388,270, dated Aug. 3, 2006.

USPTO Non-Final Office Action, U.S. Appl. No. 11/388,270, mailed Nov. 16, 2006.
USPTO Non-Final Office Action, U.S. Appl. No. 11/388,270, mailed Sep. 20, 2007.
USPTO Interview Summary, U.S. Appl. No. 11/388,270, dated Dec. 14, 2007.
USPTO Non-Final Office Action, U.S. Appl. No. 11/388,270, mailed Mar. 25, 2008.
USPTO Final Office Action, U.S. Appl. No. 11/388,270, mailed Oct. 29, 2008.
USPTO Advisory Action, U.S. Appl. No. 11/388,270, mailed Jan. 23, 2009.
USPTO Non-Final Office Action, U.S. Appl. No. 11/388,270, mailed Jul. 9, 2009.
USPTO Interview Summary, U.S. Appl. No. 11/388,270, dated Nov. 12, 2010.
USPTO Notice of Allowance and Fees Due, U.S. Appl. No. 11/388,270, mailed Jan. 5, 2011.
USPTO Non-Final Office Action, U.S. Appl. No. 11/129,839, mailed Jun. 10, 2008.
Eisenberg et al. 2004, "Efficacy, safety and pharmacokinetics of palonosetron in patients receiving highly emetogenic cisplatin-based chemotherapy: a dose-ranging clinical study. " Annals of Oncology, vol. 15, pp. 330-337.
Mayron et al. 1996, "Stability and compatibility of granistron hydrochloride in i.v. solutions and oral liquids and during simulated Y-site injection with selected drugs." Am J Health-Sys Pharm, 53: 294-304.
Trissel et al. 1997, "Compatibility of granisetron hydrochloride with selected drugs during simulated Y-site administration." Am J Health-Syst Pharm 54: 56-60.
USPTO Final Office Action, U.S. Appl. No. 11/129,839, mailed Mar. 17, 2009.
USPTO Advisory Action, U.S. Appl. No. 11/129,839, mailed Jul. 22, 2009.
USPTO Non-Final Office Action, U.S. Appl. No. 11/129,839, mailed Jan. 15, 2010.
USPTO Examiner Interview Summary, U.S. Appl. No. 11/129,839, mailed Nov. 9, 2010.
USPTO Notice of Allowance and Fees Due, U.S. Appl. No. 11/129,839, mailed Jan. 3, 2011.
USPTO Notice of Abandonment, U.S. Appl. No. 11/129,839, mailed Apr. 18, 2011.
USPTO Non-Final Office Action, U.S. Appl. No. 13/077,374, mailed Feb. 17, 2012.
Roila et al. 1998, "Prevention of chemotherapy- and radiotherapy-induced emesis: Results of the Perugia consensus conference." Annals of Oncology, vol. 9, pp. 811-819.
USPTO Final Office Action, U.S. Appl. No. 13/077,374, mailed Nov. 23, 2012.
Piraccini, Gaia et al., American Society of Clinical Oncology May 12-15, 2001 San Francisco—USA (vol. 20, part 1 of 2, 2001) (Abstract No. 1595).
USPTO Non-Final Office Action, U.S. Appl. No. 11/201,035, mailed May 16, 2008.
USPTO Final Office Action, U.S. Appl. No. 11/201,035, mailed Feb. 4, 2009.
USPTO Final Office Action, U.S. Appl. No. 11/201,035, mailed Jun. 8, 2010.
FDA approval letter of Aloxi (palonosetron hydrochloride injection), dated Jul. 25, 2003.
Macciocchi A, Chernoff SB, Gallagher SC. A phase II dose-ranging study to assess intravenous doses of palonosetron for the prevention of highly emetogenic chemotherapy-induced nausea and vomiting. In: Program/Proceedings of the 38th Annual Meeting of the American Society of Clinical Oncology; May 18-21, 2002; Orlando, Fla. Abstract 1480.
Grunberg SM, Hajdenberg J, Charu V, et al. Palonosetron is active in preventing acute and delayed emesis following moderately emetogenic chemotherapy: results of a phase III trial. Support Care Cancer 2002;10:Abstract P-113.
Aapro MS, Selak E, Lichinitser M, et al. Palonosetron is more effective than ondansetron in preventing chemotherapy-induced nausea and vomiting in patients receiving moderately emetogenic chemotherapy: results of a phase III trial. In: Program/Proceedings of the 39th Annual Meeting of the American Society of Clinical Oncology; May 31-Jun. 3, 2003; Chicago, Ill. Abstract 2918.
Aapro MS, Bertoli L, Lordick F, et al. Palonosetron is effective in preventing acute and delayed chemotherapy induced nausea and vomiting in patients receiving highly emetogenic chemotherapy. $15^{th}$ MASCC International Symposium, Berlin, Germany. Support Care Cancer, vol. 11, No. 6, Jun. 2003, A17.
Cartmell AD, Ferguson S, Yanagihara R, et al. Protection against chemotherapy-induced nausea and vomiting is maintained over multiple cycles of moderately or highly emetogenic chemotherapy by palonosetron, a potent 5 HT3 receptor antagonist. In: Program/Proceedings of the 39th Annual Meeting of the American Society of Clinical Oncology; May 31-Jun. 3, 2003; Chicago, Ill. Abstract 3041.
Sabra, Choice of a 5-HT3 Receptor Antagonist for the Hospital Formulary, EHP, Oct. 1996, vol. 2, Supp 1, S19-S24.
Gregory and Ettinger, 5HT3 receptor antagonists for the prevention of chemotherapy-induced nausea and vomiting. A comparison of their pharmacology and clinical efficacy. Drugs, Feb. 1998; 55(2): 173-189.
Full Prescribing Information for Aloxi (palonosetron HCl) injection for Intravenous Use (2008).
Drug, Dose & Schedule Recommendations for Antiemetic Regimens (American Society for Clinical Oncology) (2006).
Yamakuni, et al., The Journal of Pharmacology and Experimental Therapeutics, Probable Involvement of the 5-Hydroxytryptamine4 Receptor in Methotrexate-Induced Delayed Emesis in Dogs, 2000, The American Society for Pharmacology and Experimental Therapeutics, vol. 292, No. 3, p. 1002-1294.
Geling, et al., Should 5-Hydroxytryptamine-3 Receptor Antagonists Be Administered Beyond 24 Hours After Chemotherapy to Prevent Delayed Emesis? Systematic Re-Evaluation of Clinical Evidence and Drug Cost Implications, Journal of Clinical Oncology, vol. 23, No. 6, Feb. 20, 2005 (American Society of Clinical Oncology), pp. 1289-1294.
Rojas, et al., International Anesthesia Research Society, Palonosetron Exhibits Unique Molecular Interactions with 5-HT3 Receptor, vol. 107, No. 2, Aug. 2008, p. 469-478.
Rojas, et al., Palonosetron triggers 5-HT3 receptor internalization and causes inhibition of receptor function, European Journal of Pharmacology 626 (2010), p. 193-199.
Saito, et al., Palonosetron plus dexamethasone versus granisetron plus dexamethasone for prevention of anusea and vomiting during chemotherapy: a double-blind, double-dummy, randomised, comparative phased III trial, www.thelancet.com/oncology, vol. 10, Feb. 2009, p. 115-124.
Palonosetron: more than just another option?. www.thelancet.com/oncology, vol. 10, Feb. 2009, p. 100-101.
Lorusso, et al., Single dose of palonosetron plus dexamethasone to control nausea, vomiting and to warrant an adequate food intake in patients treated with highly emetogenic chemotherapy (HEC). Preliminary results, Support Care Cancer, published online Mar. 18, 2009.
Grunberg, et al., Effectiveness of a single-day three-drug regimen of dexamethasone, palonosetron, and aprepitant for the prevention of acute and delayed nausea and vomiting caused by moderately emetogenic chemotherapy, Support Care Cancer (2009) 17:589-594.
Celio, et al., Clinical update on palonosetron in the management of chemotherapy-induced nausea and vomiting, Tumor, 94: 447-452, 2008.
Ellebaek, et al., Optimizing antiemetic therapy in multiple-day and multiple cycles of chemotherapy, Lippincott williams & Wilkins, Current Opinion in Supportive and Palliative Care, 2008, 2:28-34.
Herrington, et al., Randomized, Placebo-controlled, Pilot Study Evaluating Aprepitant Single Dose Plus Palonosetron and Dexamethasone for the Prevention of Acute and Delayed Chemotherapy-induced Nausea and Vomiting, American Cancer Society, published online Mar. 7, 2008 in Wiley InterScience (www.interscience.wiley.com).
Massa, et al., Palonosetron plus dexamethasone effectively prevents acute and delayed chemotherapy-induced nausea and vomiting following highly or moderately emetogenic chemotherapy in pretreated patients who have failed to respond to a previous antiemetic treatment: Comparison between elderly and non-elderly patient response, Critical Reviews in Oncology/Hematology 70 (2009) 83-91.

2006 Update of the ASCO Recommendations for Antiemetics in Oncology: Guideline Summary, American Cancer Society of Clinical Oncology, Jul. 2006, www.jopasco.org.

Warr, David, Standard treatment of chemotherapy-induced emesis, Support Care Cancer, vol. 5, pp. 12-16, 1997.

Aapro, M.S., et al. A phase III, double-blind, randomized trial of palonosetron compared with ondansetron in preventing chemotherapy-induced nausea and vomiting following highly emetogenic chemotherapy. Annals of Oncology, vol. 17, pp. 1441-1449, 2006.

Eisenberg, Peter, et al. Improved Prevention of Moderately Emetogenic Chemotherapy-Induced Nausea and Vomiting with Palonosetron, a Pharmacologically Novel5-HT3 Receptor Antagonist. Cancer, vol. 98, No. 11, pp. 2473-2482, Dec. 1, 2003.

Gandara, D.R., et al. The delayed-emesis syndrome from cisplatin: Phase III evaluation of ondansetron versus placebo. Semin Oneal vol. 19, No. 4, pp. 67-71, Aug. 1992 (suppl 10).

Goedhals, L., et al. Control of delayed nausea and vomiting with granisetron plus dexamethasone or dexamethasone alone in patients receiving highly emetogenic chemotherapy: A double-blind, placebo-controlled, comparative study. Ann Oneal, vol. 9, pp. 661-666, 1998.

Gralla, R., et al. Palonosetron improves prevention of chemotherapy-induced nausea and vomiting following moderately emetogenic chemotherapy: results of a double-blind randomized phase III trial comparing single doses of palonosetron with ondansetron. Annals of Oncology, vol. 14, pp. 1570-1577, 2003.

Italian Group for Antiemetic Research. Dexamethasone alone or in combination with ondansetron for the prevention of delayed nausea and vomiting induced by chemotherapy. N Engl J Med, vol. 342, No. 21, pp. 1554-1559, May 25, 2000.

Kaizer, L., et al. Effect of schedule and maintenance on the antiemetic efficacy of ondansetron combined with dexamethasone in acute and delayed nausea and emesis in patients receiving moderately emetogenic chemotherapy: A phase III trial by the National Cancer Institute of Canada Clinical Trials Group. J Clin Oncol, vol. 12, No. 5, pp. 1050-1057, May 1994.

Latreille, J., et al. Use of dexamethasone and granisetron in the control of delayed emesis for patients who receive highly emetogenic chemotherapy: National Cancer Institute of Canada Clinical Trials Group. J Clin Oncol, vol. 16, No. 3, pp. 1174-1178, Mar. 1998.

Antiemetic Subcommittee of the Multinational Association of Supportive Care in Cancer (MCSCC). Prevention of chemotherapy- and radiotherapy-induced emesis: Results of the Perugia Consensus Conference. Annals of Oncology, vol. 9, pp. 811-819, 1998.

Moyer, Paula. New Understanding of Emesis Pathways Leading to New Treatment, Better Control. Oncology Times, vol. 25, Issue 10, pp. 48-51, May 25, 2003.

Navari, R.M., et al. Oral ondansetron for the control of cisplatin-induced delayed emesis: A large, multicenter, double-blind, randomized comparative trial of ondansetron versus placebo. J Clin Oncol,vol. 13, No. 9, pp. 2408-2416, Sep. 1995.

Olver, I., et al. A multicenter, double-blind study comparing placebo, ondansetron and ondansetron plus dexamethasone for the control of cisplatin-induced delayed emesis. Ann Oncol, vol. 7, pp. 945-952, 1996.

Pater, J.L., et al. The role of the 5-HT3 antagonists ondansetron and dolasetron in the control of delayed onset nausea and vomiting in patients receiving moderately emetogenic chemotherapy. Ann Oncol, vol. 8, pp. 181-185, 1997.

Rojas, Camilo, et al. The Antiemetic 5-HT3 Receptor Antagonist Palonosetron Inhibits Substance P-Mediated Responses in Vitro and in Vivo. J Pharmacal Exper Thera, vol. 335, No. 2, pp. 362-368, 2010.

Sorbe, B. G., et al. A study evaluating the efficacy and tolerability of tropisetron in combination with dexamethasone in the prevention of delayed platinum-induced nausea and emesis. Cancer, vol. 83, pp. 1022-1032, 1998.

Stewart, A., et al. Ondansetron Compared with Granisetron in the Prophylaxis of Cyclophosphamide-Induced Emesis in Out-Patients: A Multicentre, Double-Blind, Double-Dummy, Randomised, Parallel-Group Study. Oncology, vol. 52, pp. 202-210, 1995.

Weiderpass, Elisabete, et al. Use of an NK1 Receptor Antagonist to Prevent Delayed Emesis After Cisplatin. Journal of the National Cancer Institute, vol. 89, No. 11, pp. 817-818, Jun. 4, 1997.

Akers, Michael J., Excipient-Drug Interactions in Parenteral Formulations. Journal of Pharmaceutical Sciences, vol. 91, No. 11, Nov. 2002, pp. 2283-2300.

Maemondo, et al., A phase II study of palonosetron combined with dexamethasone to prevent nausea and vomiting induced by highly emetogenic chemotherapy. Annals of Oncology, Nov. 2009, vol. 20, No. II, pp. 1860-1866.

Program/Proceedings American Society of Clinical Oncology, vol. 20, Part 1 of 2, 2001, Abstract No. 1595 and associated poster presentation.

Saito, et al., Review of palonosetron: emerging data distinguishing it as a novel 5-HT3 receptor antagonist for chemotherapy-induced nausea and vomiting. Expert Opin. Pharmacother (2010) 11 (6), pp. 1003-1014.

MGI-HHC__SEC__filing (2001).
ROCHE0008749-876 (1995) (portions redacted).
HELSN0135068-82 (1998) (portions redacted).
English-language translation of Italian-language portions of HELSN0135068-82 (1998).
HELSN0161327-348 (2000) (portions redacted).
HELSN0138407-24 (1998) (portions redacted).
HELSN0376401-469 (2002) (portions redacted).
HELSN0392650-72 (1999) (portions redacted).
Dr. Reddy's Labs., Ltd.'s and Dr. Reddy's Labs., Inc.'s Memorandum of Law in Support of Their Motion to Amend Their Invalidity Contentions dated Feb. 15, 2013 (D.N.J. Case No. 11-3962).
HELSN0376719-21 (2001).
HELSN0376722-23 (2001).
HELSN0376724 (2002).
Dr. Reddy's Laboratories, Ltd.'s and Dr. Reddy's Laboratories, Inc.'s Redline of Proposed Amended Invalidity Contentions Pursuant to L. Pat. R. 3.6(c) filed Feb. 15, 2013 (D.N.J. Case No. 11-3962).
Dr. Reddy's Laboratories, Ltd.'s and Dr. Reddy's Laboratories, Inc.'s Reply Memorandum of Law in Further Support of Their Motion to Amend Their Invalidity Contentions dated Mar. 15, 2013 (D.N.J. Case No. 11-3962).
Teva Pharm. Indus., Ltd.'s and Teva Pharm. USA, Inc.'s Memorandum in Support of Their Motion to Amend Invalidity Contentions dated Feb. 15, 2013 (D.N.J. Case No. 1-3962).
HELSN0388553-65 (1998).
HELSN0388566-68 (1998).
HELSN0388569-74 (1998).
HELSN0388587-91 (1998).
HELSN0388592-95 (1998).
English-language translation of HELSN0388592-95 (1998).
HELSN0388596-97 (1998).
HELSN0388604 (1998).
HELSN0388605-06 (1998).
HELSN0388607-09 (1998).
HELSN0389134-44 (1999).
HELSN0389145-48 (1999).
HELSN0389149-61 (2000).
HELSN0392047-48 (1998).
HELSN0392393-94 (1998).
HELS0393657-61 (2000).
English-language translation of Italian-language portions of HELSN039657-61 (2000).
Excerpts from Calderari Deposition Transcript, pp. 1-4, 229-232, and 278-393 (2013).
HELSN0000093-9 (2006).
HELSN0004207 (2002).
HELSN0004217 (2002).
Teva Pharm. Indus., Ltd.'s and Teva Pharm. USA, Inc.'s Reply in Support of Their Motion to Amend Their Invalidity Contentions dated Mar. 15, 2013 (D.N.J. Case No. 1-3962).
HELSN00388448-542 (1998-1999).
English-language translation of Italian-language portions of HELSN00388448-542 (1998-1999) (portions redacted).

HELSN0388543-44 (1999).
HELSN0388545-52 (1998).
HELSN0388575-76 (1998).
HELSN0388577-80 (1998).
HELSN0388581-82 (1998).
HELSN0388583-84 (1998).
HELSN0388585 (1998).
HELSN0388586 (1998).
HELSN0388598-601 (1998).
HELSN0388602-03 (1998).
HELSN0388610 (1998).
Sandoz Inc.'s Redacted Memorandum of Law in Support of its Motion to Amend its Invalidity Contentions dated Feb. 15, 2013 (D.N.J. Case No. 11-3962).
Exhibit G to Sandoz Inc.'s Redacted Memorandum of Law in Support of its Motion to Amend its Invalidity Contentions dated Feb. 15, 2013 (D.N.J. Case No. 11-3962).
Sandoz Inc.'s Redacted Reply Memorandum of Law in Support of its Motion to Amend its Invalidity Contentions dated Mar. 15, 2013 (D.N.J. Case No. 11-3962).
Aurobindo Pharma Ltd. Paragraph IV notice regarding U.S. Patent Nos. 7,947,724; 7,947,725; and 7,960,424, dated Mar. 5, 2013 (D. Del. Case No. 13-688).
Complaint for patent infringement filed by Helsinn Healthcare S.A. and Roche Palo Alto LLC against Aurobindo Pharma Ltd. and Aurobindo Pharma USA Inc. dated Apr. 16, 2013 (D. Del. Case No. 13-688).
Accord Healthcare, Inc. Paragraph IV notice regarding U.S. Patent Nos. 7,947,724; 7,947,725; and 7,960,424, dated Apr. 3, 2013.

LIQUID PHARMACEUTICAL FORMULATIONS OF PALONOSETRON

The present application is a continuation of U.S. Ser. No. 11/186,311 filed Jul. 21, 2005 (allowed), which is a continuation of PCT/EP04/000888, filed Jan. 30, 2004, which claims priority to U.S. Provisional Application 60/444,351, filed Jan. 30, 2003. The content of these applications is incorporated herein by reference.

FIELD OF THE INVENTION

The present invention relates to shelf-life stable liquid formulations of palonosetron that are especially useful in the preparation of injectable and oral medicaments.

BACKGROUND OF THE INVENTION

Emesis is a devastating consequence of cytotoxic therapy, radiotherapy, and post-operative environments that drastically affects the quality of life of people undergoing such treatments. In recent years a class of drugs referred to as 5-$HT_3$ (5-hydroxytryptamine) receptor antagonists has been developed that treat such emesis by antagonizing cerebral functions associated with the 5-$HT_3$ receptor. See *Drugs Acting on 5-Hydroxytryptamine Receptors*: The Lancet Sep. 23, 1989 and references cited therein. Drugs within this class include ondansetron, granisetron, alosetron, tropisetron, and dolasetron. These 5-$HT_3$ antagonists are often administered intravenously shortly before chemotherapy or radiotherapy is initiated, and can be administered more than once during a cycle of chemotherapy or radiotherapy. In addition, they are often supplied as tablets or oral elixirs to either supplement an intravenous administration, or to ease home usage of the drug if the patient is self-administering the chemotherapeutic regimen.

Because some chemotherapeutic agents can induce emesis over extended periods of several days even when they are administered only once, it would be desirable to administer an emesis-inhibiting drug such as a 5-$HT_3$ antagonist every day until the risk of emesis has substantially subsided. The present class of 5-$HT_3$ antagonists has not proven especially helpful meeting this need, however, because the 5-$HT_3$ receptor antagonists currently marketed have proven to be less effective in controlling delayed nausea and vomiting than they are at controlling acute emesis. Sabra, K, *Choice of a 5HT$_3$ Receptor Antagonist for the Hospital Formulary*. EHP, October 1996; 2 (suppl 1):S19-24.

Recently, clinical investigations have been made concerning palonosetron, a new 5-$HT_3$ receptor antagonist reported in U.S. Pat. No. 5,202,333. These investigations have shown that the drug is an order of magnitude more potent than most existing 5-$HT_3$ receptor antagonists, has a surprising half-life of about 40 hours, and is effective to reduce delayed-onset nausea induced by chemotherapeutic agents. However, formulating palonosetron in liquid formulations has not proven an easy task, typically due to shelf-stability issues. U.S. Pat. No. 5,202,333 discloses an intravenous formulation of palonosetron in example 13 that contains the following ingredients:

| Ingredient | Mg |
|---|---|
| Palonosetron HCl | 10-100 mg. |
| Dextrose Monohydrate | q.s. to make Isotonic |
| Citric Acid Monohydrate | 1.05 mg. |
| Sodium Hydroxide | 0.18 mg. |
| WFI | To 1.0 ml. |

The formulation has a pH of 3.7 and a shelf stability of less than the 1-2 year time period required by health authorities in various countries.

Ondansetron, its uses, and medicaments made with ondansetron are disclosed in U.S. Pat. Nos. 4,695,578, 4,753,789, 4,929,632, 5,240,954, 5,344,658, 5,578,628, 5,578,632, 5,922,749, 5,622,720, 5,955,488, and 6,063,802. Commercially it is distributed by GlaxoSmithKline as Zofran® and is indicated for prevention of postoperative nausea and vomiting (PONV), cancer chemotherapy-induced nausea and vomiting (CINV), and radiotherapy-induced nausea and vomiting (RINV) and it is available as an injection, tablets and solution, and as Zofran ODT® (ondansetron) Orally Disintegrating Tablets.

Granisetron, its uses, and medicaments made with granisetron are disclosed in U.S. Pat. Nos. 4,886,808, 4,937,247, 5,034,398 and 6,294,548. Commercially it is distributed by Roche Laboratories Inc. as Kytril®, indicated for the prevention of nausea and vomiting associated with chemotherapy or radiation therapy, and is offered in tablet form, oral solution, and as an injection.

Alosetron, its uses, and medicaments made with alosetron are disclosed in U.S. Pat. Nos. 5,360,800 and 6,284,770. Commercially it is distributed by GlaxoSmithKline as Lotronex®.

Tropisetron is commercially available as Navoban® (Novartis) CAS-89565-68-4 (tropisetron); CAS-105826-92-4 (tropisetron hydrochloride) and it is indicated for treatment of PONV and CINV.

Dolasetron, its uses, and medicaments made with ondansetron are disclosed in U.S. Pat. Nos. 5,011,846, and 4,906,755. Commercially it is distributed by Aventis Pharmaceuticals Inc. as Anzemet®, indicated for prevention of both PONV and CINV, and it is offered in the form of a tablet or an intravenous solution.

Therefore, there exists a need for a palonosetron formulation with increased stability and thereby increased shelf life. There also exists a need for an appropriate range of concentrations for both the 5-$HT_3$ receptor antagonist and its pharmaceutically acceptable carriers that would facilitate making a formulation with this increased stability.

It is an object of the present invention to provide a formulation of Palonosetron hydrochloride with increased pharmaceutical stability for preventing and/or reducing emesis.

It is another object of the invention to provide an acceptable range of concentrations which will stabilize a formulation containing Palonosetron hydrochloride.

It is a further object of the invention to provide a formulation of Palonosetron which would allow for prolonged storage.

It is also an object of the invention to provide a formulation of Palonosetron which would allow terminal sterilization.

SUMMARY OF THE INVENTION

The inventors have made a series of discoveries that support a surprisingly effective and versatile formulation for the treatment and prevention of emesis using palonosetron. These formulations are shelf stable for periods greater than 24 months at room temperature, and thus can be stored without refrigeration, and manufactured using non-aseptic, terminal sterilization processes.

In one aspect, the inventors have discovered that formulations which include the active ingredient palonosetron require in some instances only $1/10^{th}$ the amount of other previously known compounds for treating emesis, which surprisingly allows the use of concentrations of palonosetron far below those that would ordinarily be expected. Thus, in one embodiment the invention provides a pharmaceutically stable solution for preventing or reducing emesis comprising a) from about 0.01 mg/mL to about 5 mg/mL palonosetron or a pharmaceutically acceptable salt thereof; and b) a pharmaceutically acceptable carrier.

The inventors have further discovered that by adjusting the formulation's pH and/or excipient concentrations it is possible to increase the stability of palonosetron formulations. Therefore, in another embodiment, the invention provides a pharmaceutically stable solution for preventing or reducing emesis comprising a) palonosetron or a pharmaceutically acceptable salt thereof; and b) a pharmaceutically acceptable carrier, at a pH from about 4.0 to about 6.0. In another embodiment the invention provides a pharmaceutically stable solution for preventing or reducing emesis comprising from about 0.01 to about 5.0 mg/ml palonosetron or a pharmaceutically acceptable salt thereof; from about 10 to about 100 millimoles citrate buffer; and from about 0.005 to about 1.0 mg/ml EDTA.

The inventors have further discovered that the addition of mannitol and a chelating agent can increase the stability of palonosetron formulations. Therefore, in still another embodiment the invention provides a pharmaceutically stable solution for preventing or reducing emesis comprising a) palonosetron or a pharmaceutically acceptable salt thereof and b) a pharmaceutically acceptable carrier, wherein the pharmaceutically acceptable carrier comprises a chelating agent and mannitol.

DETAILED DESCRIPTION OF THE INVENTION

Definitions

"Vial" means a small glass container sealed with the most suitable stopper and seal, other suitable primary containers may be used, for instance, but not limited to, pre-filled syringes. Vial also means a sealed container of medication that is used one time only, and includes breakable and non-breakable glass vials, breakable plastic vials, miniature screw-top jars, and any other type of container of a size capable of holding only one unit dose of palonosetron (typically about 5 mls.).

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps "Palonosetron" means (3aS)-2,3,3a,4,5,6-Hexahydro-2-[(S)-1-Azabicyclo[2.2.2]oct-3-yl]2,3,3a,4,5,6-hexahydro-1-oxo-1Hbenz[de]isoquinoline, and is preferably present as the monohydrochloride. Palonosetron monohydrochloride can be represented by the following chemical structure:

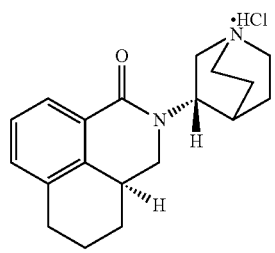

Concentrations—When concentrations of palonosetron are given herein, the concentration is measured in terms of the weight of the free base. Concentrations of all other ingredients are given based on the weight of ingredient added to the solution.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Discussion

The fact that palonosetron can be formulated in some instances at concentrations of only about $1/10^{th}$ the amount of other previously known compounds for treating emesis, surprisingly allows the use of concentrations of palonosetron far below those that would ordinarily be expected. Thus, in one embodiment the invention provides a pharmaceutically stable solution for preventing or reducing emesis comprising a) from about 0.01 mg/mL to about 5 mg/mL palonosetron or a pharmaceutically acceptable salt thereof; and b) a pharmaceutically acceptable carrier. Similarly, in another embodiment the invention provides a method of formulating a pharmaceutically stable solution of palonosetron comprising admixing from about 0.01 mg/mL to about 5 mg/mL palonosetron or a pharmaceutically acceptable salt thereof; with a pharmaceutically acceptable carrier. In alternative embodiments, the formulation includes palonosetron or a pharmaceutically acceptable salt thereof in a concentration from about 0.02 mg/mL, to about 1.0 mg/mL, from about 0.03 mg/mL to about 0.2 mg/mL, and most optimally about 0.05 mg/ml.

A particular advantage associated with the lower dosages of intravenous palonosetron is the ability to administer the drug in a single intravenous bolus over a short, discrete time period. This time period generally extends from about 10 to about 60 seconds, or about 10 to about 40 seconds, and most preferably is about 10 to 30 seconds. In one particular embodiment the palonosetron is supplied in vials that comprise 5 ml. of solution, which equates to about 0.25 mg of palonosetron at a concentration of about 0.05 mg/ml.

The inventors have further discovered that by adjusting the formulation's pH and/or excipient concentrations it is possible to increase the stability of palonosetron formulations. Therefore, in another embodiment, the invention provides a pharmaceutically stable solution for preventing or reducing emesis comprising a) palonosetron or a pharmaceutically acceptable salt thereof; and b) a pharmaceutically acceptable carrier, at a pH from about 4.0 to about 6.0. Similarly, in another embodiment the invention provides a method of formulating a pharmaceutically stable solution of palonosetron comprising admixing a) palonosetron or a pharmaceutically acceptable salt thereof; and b) a pharmaceutically acceptable carrier, at a pH from about 4.0 to about 6.0. In alternative embodiments, the pH is from about 4.5 to about 5.5, and most optimally about 5.0. There are many examples to those of skill in the art of suitable solutions to adjust the pH of a formulation. Two exemplary solutions are sodium hydroxide and hydrochloric acid solution, either of which could be used to adjust the pH of the formulation.

In another embodiment the invention provides a pharmaceutically stable solution for preventing or reducing emesis comprising from about 0.01 to about 5.0 mg/ml palonosetron or a pharmaceutically acceptable salt thereof and (i) from about 10 to about 100 millimoles citrate buffer, and/or (ii) from about 0.005 to about 1.0 mg/ml EDTA. Similarly, in another embodiment the invention provides a method of formulating a pharmaceutically stable solution of palonosetron comprising admixing from about 0.01 to about 5.0 mg/ml palonosetron or a pharmaceutically acceptable salt thereof and (i) from about 10 to about 100 millimoles citrate buffer, and/or (ii) from about 0.005 to about 1.0 mg/ml EDTA. The citrate buffer can be in the form of citric acid and/or a salt of citric acid such as trisodium citrate. In various embodiments, the ranges of one or more of the foregoing ingredients can be modified as follows:

The formulation may comprise palonosetron or a pharmaceutically acceptable salt thereof in a concentration from about 0.02 mg/mL to about 1.0 mg/mL, from about 0.03 mg/mL to about 0.2 mg/mL palonosetron hydrochloride, and most optimally about 0.05 mg/ml.

The formulation may comprise citrate buffer in a concentration of from about 10 to about 40 millimoles, or 15-30 millimoles.

The formulation may comprise EDTA in a concentration of from about 0.005 mg/ml to about 1.0 mg/ml, or about 0.3 to about 0.7 mg/ml, and most optimally about 0.5 mg/ml.

The inventors have further discovered that the addition of mannitol and a chelating agent can increase the stability of palonosetron formulations. Therefore, in still another embodiment the invention provides a pharmaceutically stable solution for preventing or reducing emesis comprising a) palonosetron or a pharmaceutically acceptable salt thereof and b) a pharmaceutically acceptable carrier, wherein the pharmaceutically acceptable carrier comprises a chelating agent and mannitol. Similarly, in another embodiment the invention provides a method of formulating a pharmaceutically stable solution of palonosetron comprising admixing a) palonosetron or a pharmaceutically acceptable salt thereof and b) a pharmaceutically acceptable carrier, wherein the pharmaceutically acceptable carrier comprises a chelating agent and mannitol. The chelating agent is preferably EDTA, and, in various embodiments the chelating agent is present in a concentration of from about 0.005 to about 1.0 mg/mL or from about 0.05 mg/mL to about 1.0 mg/mL or from about 0.3 to about 0.7 mg/ml, or most optimally about 0.5 mg/ml. In various embodiments the mannitol is present in a concentration of from about 10.0 mg/ml to about 80.0 mg/ml, from about 20.0 mg/mL to about 60.0 mg/ml, or from about 40.0 to about 45.0 mg/ml.

Injectable formulations are typically formulated as aqueous solutions in which water is the primary excipient. Oral formulations will differ from injectable formulations generally by the additional presence of flavoring agents, coloring agents, or viscosity agents. Natural or synthetic sweeteners include, among others, mannitol, sorbitol, saccharose, saccharine, aspartame, acelsulphame K, or cyclamate. These agents are generally present in concentrations in excess of 100 mg/ml or 250 mg/ml when used as sweetening agents, in contrast to the 41.5 mg/ml concentration of mannitol described in some of the embodiments of the invention, in which mannitol is acting simply as a tonicifying agent.

The formulations of the present invention are particularly suited for use in injectable and oral liquid formulations, but it will be understood that the solutions may have alternative uses. For example, they may be used as intermediates in the preparation of other pharmaceutical dosage forms. Similarly, they may have other routes of administration including intranasal or inhalation. Injectable formulations may take any route including intramuscular, intravenous or subcutaneous.

Still further embodiments relate to improvements in the ease with which the palonosetron formulation can be stored or manufactured. In particular, the inventors have discovered that the formulations of the present invention allow storage of the product for extended periods at room temperature. Thus, in yet another embodiment the invention provides a method of storing one or more containers in which are contained a solution of palonosetron or a pharmaceutically acceptable salt thereof comprising: a) providing a room comprising said one or more containers; b) adjusting or maintaining the temperature of the room at greater than about ten, 15, or 20 degrees celcius; and e) storing said containers in said room for one month, 3 months, 6 months, one year, 18 months, 24 months or more (but preferably not exceeding 36 months), wherein (i) the palonosetron or pharmaceutical salt thereof is present in a concentration of from about 0.01 mg/mL to about 5.0 mg/mL, (ii) the pH of the solution is from about 4.0 to about 6.0, (iii) the solution comprises from about 0.01 to about 5.0 mg/ml palonosetron or a pharmaceutically acceptable salt thereof, from about 10 to about 100 millimoles citrate buffer and from about 0.005 to about 1.0 mg/ml EDTA, (iv) the solution comprises a chelating agent, or (v) the solution comprises from about 10 to about 100 milliMoles of a citrate buffer.

The stability of the foregoing formulations also lends itself well to terminal sterilization processes in the manufacturing process. Therefore, in still another embodiment the invention provides a method of filling a container in which is contained a solution of palonosetron or a pharmaceutically acceptable salt thereof comprising: a) providing one or more sterile open containers (preferably 5 ml. vials); h) filling said containers with a solution of palonosetron in a non-aseptic environment; c) sealing said filled containers; and d) sterilizing said sealed, filled containers, wherein (i) the palonosetron or pharmaceutical salt thereof is present in a concentration of from about 0.01 mg/mL to about 5 mg/mL, (ii) the pH of the solution is from about 4.0 to about 6.0, (iii) the solution comprises from about 0.01 to about 5.0 mg/ml palonosetron or a pharmaceutically acceptable salt thereof, from about 10 to about 100 millimoles citrate buffer and from about 0.005 to about 1.0 mg/ml EDTA, (iv) the solution comprises a chelating agent, or (v) the solution comprises from about 10 to about 100 milliMoles of a citrate buffer.

EXAMPLES

Example 1

Stabilizing pH

A study was conducted to determine the effect of pH on formulations containing palonosetron hydrochloride, measuring the stability at 80° C. at pH 2.0, 5.0, 7.4, and 10.0. The results indicated that palonosetron hydrochloride is most stable at pH 5.0.

Example 2

Stabilizing Concentration Ranges

A formulation optimization study was performed using an experimental design software. Twenty-four lots of drug product were analyzed to investigate the appropriate concentration ranges for palonosetron hydrochloride (0.05 mg/mL to 5.0 mg/mL), citrate buffer (0 to 80 mM) and EDTA (0 to 0.10%). The level of EDTA and citrate buffer were selected based on the optimal formulation, which was shown to be formulated with EDTA 0.05% and 20 mM citrate buffer at pH 5.0. The results of this study indicated that palonosetron concentration was also a critical factor in chemical stability, with greatest stability seen at the lowest palonosetron concentrations.

Example 3

Tonicifying Agent

Formulations of palonosetron hydrochloride in citrate buffer were prepared including either a) sodium chloride or b) mannitol. The palonosetron hydrochloride formulation including mannitol showed superior stability. The optimum level of mannitol required for an isotonic solution was found to be 4.15%.

Example 4

Formulation I

The following is a representative pharmaceutical formulation containing palonosetron that is useful for intravenous formulations, or other liquid formulations of the drug.

| Ingredient | mg/mL |
| --- | --- |
| Palonosetron Hydrochloride | 0.05* |
| Mannitol | 41.5 |
| EDTA | 0.5 |
| Trisodium citrate | 3.7 |
| Citric acid | 1.56 |
| WFJ | q.s. to 1 ml |
| Sodium hydroxide solution and/or hydrochloric acid solution | pH 5.0 ± 0.5 |

*calculated as a free base

Example 5

Formulation II

The following is a representative pharmaceutical formulation containing palonosetron that is useful for oral formulations, or other liquid formulations of the drug.

| Ingredient | mg/mL |
| --- | --- |
| Palonosetron Hydrochloride | 0.05* |
| Mannitol | 150 |
| EDTA | 0.5 |
| Trisodium citrate | 3.7 |
| Citric acid | 1.56 |
| WFJ | q.s. to 1 ml |
| Sodium hydroxide solution and/or hydrochloric acid solution | pH 5.0 ± 0.5 |
| Flavoring | q.s. |

*calculated as a free base

Example 6

Stability of Palonosetron without Dexamethasone

The physical and chemical stability of palonosetron HCl was studies in concentrations of 5 µg/mL and 30 µg/mL in 5% dextrose injection, 0.9% sodium chloride injection, 5% dextrose in 0.45% sodium chloride injection, and dextrose 5% in lactated Ringer's injection. The admixtures were evaluated over 14 days at 4° C. in the dark and for 48 hours at 23° C. under fluorescent light.

Test samples of palonosetron HCl were prepared in polyvinyl chloride (PVC) bags of the infusion solutions at concentrations of 5 and 30 µg/ml. Evaluations for physical and chemical stability were performed on samples taken initially and after 1, 3, 5, 7, and 14 days of storage at 4° C. and after 1, 4, 24, and 48 hours at 23° C. Physical stability was assessed using visual observation in normal room light and using a high-intensity monodirectional light beam. In addition, turbidity and particle content were measured electronically. Chemical stability of the drug was evaluated by using a stability-indicating high performance liquid chromatographic (HPLC) analytical technique.

All samples were physically stable throughout the study. The solution remained clear, and little or no change in particulate burden and haze level were found. Additionally, little or no loss of palonosetron HCl occurred in any of the samples at either temperature throughout the entire study period.

Example 7

Stability of Palonosetron with Dexamethasone

The physical and chemical stability of palonosetron HCl 0.25 mg admixed with dexamethasone (as sodium phosphate)

10 mg or 20 mg in 5% dextrose injection or 0.9% sodium chloride injection in polyvinyl chloride (PVC) minibags, and also admixed with dexamethasone (as sodium phosphate) 3.3 mg in 5% dextrose injection or 0.9% sodium chloride injection in polypropylene syringes at 4° C. in the dark for 14 days and at 23° C. exposed to normal laboratory fluorescent light over 48 hours, was studied.

Test samples of palonosetron HCl 5 μg/mL with dexamethasone (as sodium phosphate) 0.2 mg/mL and also 0.4 mg/mL were prepared in polyvinyl chloride (PVC) minibags of each infusion solution. Additionally, palonosetron HCl 25 μg/mL with dexamethasone (as sodium phosphate) 0.33 mg/mL in each infusion solution were prepared as 10 mL of test solution in 20-mL polypropylene syringes. Evaluations for physical and chemical stability were performed on samples taken initially and after 1, 3, 7, and 14 days of storage at 4° C. and after 1, 4, 24, and 48 hours at 23° C. Physical stability was assessed using visual observation in normal room light and using a high-intensity monodirectional light beam. In addition, turbidity and particle content were measured electronically. Chemical stability of the drug was evaluated by using a stability-indicating high performance liquid chromatographic (HPLC) analytical technique.

All samples were physically compatible throughout the study. The solutions remained clear, and little or no change in particulate burden and haze level were found. Additionally, little or no loss of palonosetron HCl and dexamethasone occurred in any of the samples at either temperature throughout the entire study period.

This invention has been described with reference to its preferred embodiments. Variations and modifications of the invention will be obvious to those skilled in the art from the foregoing detailed description of the invention.

What is claimed is:

1. A method of manufacturing and terminally sterilizing a finished single unit dose vial of palonosetron or a pharmaceutically acceptable salt thereof comprising: a) providing one or more sterile open containers; b) filling said containers with a pharmaceutically stable solution of palonosetron or a pharmaceutically acceptable salt thereof; c) sealing said filled containers; d) terminally sterilizing said sealed, filled containers; and e) optionally adjusting the pH of said solution using HCl or NaOH prior to step (c), wherein the pharmaceutically stable solution has a pH of from about 4.0 to about 6.0 and comprises palonosetron hydrochloride in a concentration of from about 0.03 mg/mL to about 0.2 mg/mL based on the weight of the free base, an aqueous carrier, and a tonicity agent, and wherein the pharmaceutically stable solution optionally comprises one or a combination of mannitol, a chelating agent, and a citrate buffer.

2. The method of claim 1, wherein said solution comprises 0.05 mg/ml of palonosetron hydrochloride based on the weight of the free base.

3. The method of claim 1, wherein said solution comprises HCl or NaOH as a pH adjusting agent.

4. The method of claim 1, wherein said solution has a pH of from 4.5 to 5.5, HCl or NaOH as a pH adjusting agent, and mannitol.

5. A single unit dose of palonosetron hydrochloride made by the method of claim 4.

6. The method of claim 1, wherein said solution has a pH of from 4.5 to 5.5, HCl or NaOH as a pH adjusting agent, a chelating agent and mannitol.

7. A single unit dose of palonosetron hydrochloric made by the method of claim 6.

8. The method of claim 1, wherein said solution comprises HCl or NaOH as a pH adjusting agent, a chelating agent and mannitol.

9. The method of claim 1, wherein said solution comprises a chelating agent and mannitol.

10. The method of claim 1, wherein said solution comprises a chelating agent.

11. The method of claim 1, wherein said solution comprises mannitol.

12. A single unit dose of palonosetron hydrochloride made by the method of claim 1.

* * * * *